US00PP15178P2

(12) United States Plant Patent
Winwood

(10) Patent No.: US PP15,178 P2
(45) Date of Patent: Sep. 28, 2004

(54) ***ABELIA* PLANT NAMED 'SAXON GOLD'**

(50) Latin Name: *Abelia schumanii*
Varietal Denomination: Saxon Gold

(76) Inventor: Garry Winwood, Saxon Nursery, Hankham, Pervensey, East Sussex BN24 5AP (GB)

( * ) Notice: Subject to any disclaimer, the term of this patent is extended or adjusted under 35 U.S.C. 154(b) by 31 days.

(21) Appl. No.: 10/442,593

(22) Filed: May 20, 2003

(51) Int. Cl.[7] ..... A01H 5/00
(52) U.S. Cl. ..... Plt./226
(58) Field of Search ..... Plt./226

(56) References Cited

PUBLICATIONS

GTITM UPOVROM Citation for 'Saxon Gold' as per GB PBR 02300290; May 24, 2001.*

* cited by examiner

*Primary Examiner*—Kent Bell

(57) ABSTRACT

A new cultivar of *Abelia* named 'Saxon Gold' that is characterized by golden-yellow foliage and a profusion of pale violet flowers in summer. In combination these traits set 'Saxon Gold' apart from all other existing varieties of *Abelia* known to the inventor.

2 Drawing Sheets

Genus: *Abelia.*
Species: *schumanii.*
Denomination: Saxon Gold.

BACKGROUND OF THE INVENTION

The present invention relates to a new and distinct cultivar of *Abelia* grown as an ornamental for use in the landscape. The new cultivar is known botanically as *Abelia schumanii* and will be referred to hereinafter by the cultivar name 'Saxon Gold'.

The inventor discovered 'Saxon Gold' as an individual chance hybrid seedling found in and among a crop of potted *Abelia schumanii* in a cultivated area of the Inventor's nursery in Sussex, England. The inventor selected 'Saxon Gold' in 1997 based on the distinguishing traits of golden-yellow foliage, reddish stems, and high flower count in summer.

The parent plants are presumed to be *Abelia* hybrids. The female parent is an *Abelia schumanii* (unpatented) hybrid and the male parent is an unidentified *Abelia* hybrid. 'Saxon Gold' is distinguishable from the female parent plant by golden-yellow foliage and reddish stems.

There are no close comparison plants known to the inventor. When compared to *Abelia* 'Francis Mason' (unpatented) and *Abelia* 'Sunrise' (U.S. Plant Pat. No. 9,698), 'Saxon Gold' differs from both in golden-yellow foliage, reddish stems, and high flower count in summer.

Saxon Gold produces and maintains golden-yellow foliage under its recommended conditions of good sunlight, or under part-sun/part-shade conditions which may arise under a light canopy of surrounding taller plant material. Under conditions of permanent shade, the older foliage may turn to a lime-green coloration, which coloration may also arise within the center of the plant itself when the outer golden-yellow growth exerts shade over older previously golden-yellow foliage.

'Saxon Gold' was first asexually propagated at the Inventor's nursery in April 1997 under the direct supervision of the inventor. Asexual propagation was accomplished using tip and stem cuttings. The Inventor has since determined that Saxon Gold reproduces true to type in successive generations of asexual reproduction. Propagation can also be accomplished using semi-ripe cuttings.

The Inventor made application for a grant of United Kingdom Plant Breeder's Rights which was published in the June 2001 Official Gazette of the United Kingdom Plant Breeder's Rights Office as Application No. AFP 23/290, and Date of Application May 18, 2001. A grant of United Kingdom Plant Breeder's Rights was published in the June 2003 Official Gazette of the United Kingdom Plant Breeder's Rights Office, as Grant No. 7546, and Date of Grant May 19, 2003. The first distribution to any public took place on May 22, 2002 on which date the Inventor first displayed and put on sale plants of the variety at Inventor's own garden center.

SUMMARY OF THE INVENTION

The following represent the distinguishing characteristics of the new *Abelia* cultivar 'Saxon Gold'. In combination these traits set 'Saxon Gold' apart from all other existing varieties of *Abelia* known to the inventor. 'Saxon Gold' has not been tested under all possible conditions and phenotypic differences may be observed with variations in environmental, climatic, and cultural conditions, however, without any variance in genotype.

1. *Abelia* 'Saxon Gold' exhibits golden-yellow young foliage.
2. *Abelia* 'Saxon Gold' is 1.2 meters in height and 1 meter in width at maturity.
3. *Abelia* 'Saxon Gold' exhibits pale violet flowers.
4. *Abelia* 'Saxon Gold' exhibits reddish stems.
5. *Abelia* 'Saxon Gold' is suitable for use as a container or landscape plant.
6. *Abelia* 'Saxon Gold' is hardy to minus 10° Centigrade.
7. *Abelia* 'Saxon Gold' is floriferous.

BRIEF DESCRIPTION OF THE DRAWINGS

The accompanying color drawings illustrate the overall appearance of the new *Abelia* cultivar 'Saxon Gold' showing the colors as true as it is reasonably possible to obtain in colored reproductions of this type. Colors in the photographs may differ from the color values cited in the detailed botanical description, which accurately describe the actual colors of the new variety 'Saxon Gold'. The plants in the photographs are in 5-liter containers that are 18-months-old and grown out-of-doors in Azusa, Calif. The drawing on sheet 1 illustrates the entire plant. The drawing on sheet 2 illustrates the flower. Both drawings depict the lime green coloration of the older foliage within the center of the plant. The photographs were taken using conventional techniques and although foliage colors may appear different from actual colors due to light reflectance, they are as accurate as possible by conventional photography.

BOTANICAL DESCRIPTION OF THE PLANT

The following is a detailed description of the *Abelia* cultivar named 'Saxon Gold'. Data was collected in Arroyo Grande, Calif. from plants that are 18-months-old and grown in 5-liter containers out-of-doors. Color determinations are in accordance with The Royal Horticultural Society Colour Chart 2001 edition except where general color terms of ordinary dictionary significance are used. 'Saxon Gold' has not been tested under all possible conditions and phenotypic differences may be observed with variations in environmental, climatic, and cultural conditions, however, without any variance in genotype. The growing requirements are similar to the species.

Botanical classification: *Abelia* 'Saxon Gold'.
Species: *schumanii.*
Uses: Ornamental landscape for specimen, borders or container plant.
Parent: 'Saxon Gold' is a chance sport that resulted from Parent plant: Presumed to be *Abelia schumanii.*
Type: Dwarf shrub.
Vigor: Medium vigor.
Habit: Compact.
Form: Bushy mound.
Height: 26 cm. in height in a 5-liter container and 1.2 meters in height at maturity.
Width: 64 cm. in a 5-liter container and 1 meter in width at maturity.
Hardiness: Hardy to minus 10° Centigrade.
Propagation: Soft and semi-ripe cuttings.
Root system: Fibrous.
Soil: Well-drained humus rich soil. 5.5 ph is ideal.
Sunlight: Good amount of light or dappled shade. Not full midday sun if plant is dry.
Time to initiate roots: 4–6 weeks are needed for an initial cutting to produce roots at ideal temperatures of 16–26° Centigrade, but temperatures can be lower.
Crop time: 6–9 months are needed to produce a finished 1-liter container from a rooted cutting.
Seasonal interest: Pale violet flowers.
Diseases and pests: Susceptible to white fly under protection and Botrytis on flowers when grown under glass.
Potential growing problems: Young foliage may scorch in very bright, hot conditions.
Stems:
- *Branching habit.*—Densely branched with arching and spreading branches.
- *Internode length.*—1.75 cm. between nodes.
- *Stem diameter.*—1 mm. in diameter.
- *Stem length.*—17 cm. in length.
- *Shape.*—Cylindrical.
- *Surface.*—Pubescent.
- *Stem color.*—172A.

Foliage:
- *Type.*—Evergreen to semi-evergreen.
- *Leaf arrangement.*—Opposite.
- *Leaf division.*—Simple.
- *Margins* (*young and mature leaves*).—Entire and puberulent.
- *Leaf shape* (*young and mature*).—Ovate.
- *Leaf base* (*young and mature*).—Rounded.
- *Leaf apex* (*young and mature*).—Acute.
- *Leaf venation* (*young and mature*).—Pinnate.
- *Vein color for young and mature leaves* (*adaxial surface*).—162C.
- *Vein color for young and mature leaves* (*abaxial surface*).—162C.
- *Young leaf surface* (*adaxial*).—Puberulent.
- *Young leaf surface* (*abaxial*).—Puberulent.
- *Mature leaf surface* (*adaxial*).—Glossy and slightly puberulent.
- *Mature leaf surface* (*abaxial*).—Matte and slightly puberulent.
- *Leaf attachment.*—Petiolate.
- *Petiole dimensions* (*young and mature leaves*).—3 mm. in length and 1 mm. in diameter.
- *Petiole color.*—172C.
- *Petiole shape.*—Cylindrical.
- *Petiole surface.*—Puberulent.
- *Mature leaf dimensions.*—2 cm. in length and 1.25 cm. in width.
- *Young leaf dimensions.*—7 mm. in length and 4 mm. in width.
- *Mature leaf color* (*adaxial surface*).—162B.
- *Mature leaf color* (*abaxial surface*).—162C.
- *Young leaf color* (*adaxial surface*).—162B.
- *Young leaf color* (*abaxial surface*).—162C.
- *Mature leaf color in shade* (*both surfaces*).—Yellow-green range, varying between N144A and 144A.
- *Foliar fragrance.*—None observed.

Flower:
- *Inflorescence.*—Terminal cymes.
- *Number of flowers.*—4–12 flowers per cyme.
- *Number of cymes.*—Approximately 14 cymes per 5-liter container.
- *Inflorescence dimensions.*—3 cm. in length and 6 cm. in width.
- *Persistent or self-cleaning.*—Self cleaning.
- *Pedicel color.*—172C.
- *Pedicel dimensions.*—6 mm. in length and 2 mm. in width.
- *Pedicel surface.*—Pubescent.
- *Pedicel shape.*—Cylindrical and furrowed.
- *Shape of flower.*—Tubular to funnel.
- *Flower color.*—76B.
- *Aspect.*—Facing outward.
- *Bud shape.*—Ovate.
- *Bud color.*—152C.
- *Bud surface.*—Glabrous.
- *Bud dimensions.*—5 mm. in length and 3 mm. in diameter.
- *Flower dimensions.*—2.25 cm. in length and 1.75 cm. in width at widest part.

*Corolla tube depth.*—1.25 cm in depth.
*Corolla tube surface* (*inner surface*).—Pubescent.
*Corolla tube surface* (*outer surface*).—Glabrous.
*Corolla tube color.*—76B.
*Corolla tube shape.*—Funnelform and slightly inflated.
*Lobes.*—Five in number.
*Color of lobes.*—76B.
*Lobe apex.*—Rounded.
*Dimensions of lobe.*—6 mm. in length and 6 mm. in width.
*Calyx color.*—173C.
*Surface of calyx.*—Glabrous.
*Sepals.*—Two to three in number.
*Sepal color.*—173C.
*Sepal surface.*—Glabrous.
*Fused or unfused.*—Unfused.
*Persistent or self-cleaning.*—Persistent.
*Sepal apex.*—Rounded to Emarginate.
*Sepal dimensions.*—9 mm. in length and 6 mm. in width.
*Blooming period.*—Late spring, summer and fall.
*Fragrance.*—Sweet honeysuckle-like scent.

Reproduction organs:

*Stamens.*—Four attached to base of corolla tube.
*Type.*—Didynamous.
*Stamen shape.*—Filament.
*Dimensions of stamen.*—2 are 12 mm. in length and less than 0.50 mm. in width, and 2 are 17 mm. in length and less than 0.50 mm. in width.
*Color of stamen filament.*—155A.
*Dimensions of anther.*—0.25 mm. in width and 2 mm. in length.
*Pollen color.*—155A.
*Amount of pollen.*—Moderate amount.
*Anther color.*—155A.
*Pistil.*—One.
*Color of pistil.*—155A.
*Pistil shape.*—Filament.
*Dimensions of pistil.*—18 mm. in length and less than 0.50 mm. in diameter.
*Style shape.*—Elongate.
*Stigma shape.*—Bulbous.
*Ovary position.*—Inferior.
*Ovary color.*—155A.
*Ovary shape.*—Oblong.
*Ovary dimensions.*—2 mm. in diameter and 5 mm. in length.

Seed: No seed has been observed to date.

I claim:

1. A new and distinct variety of *Abelia* plant named 'Saxon Gold' as described and illustrated.

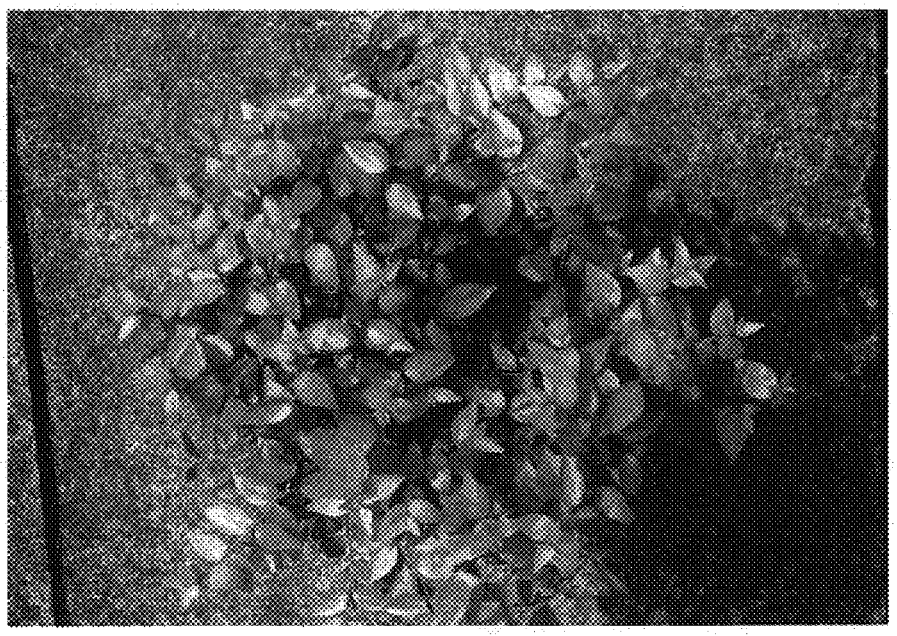

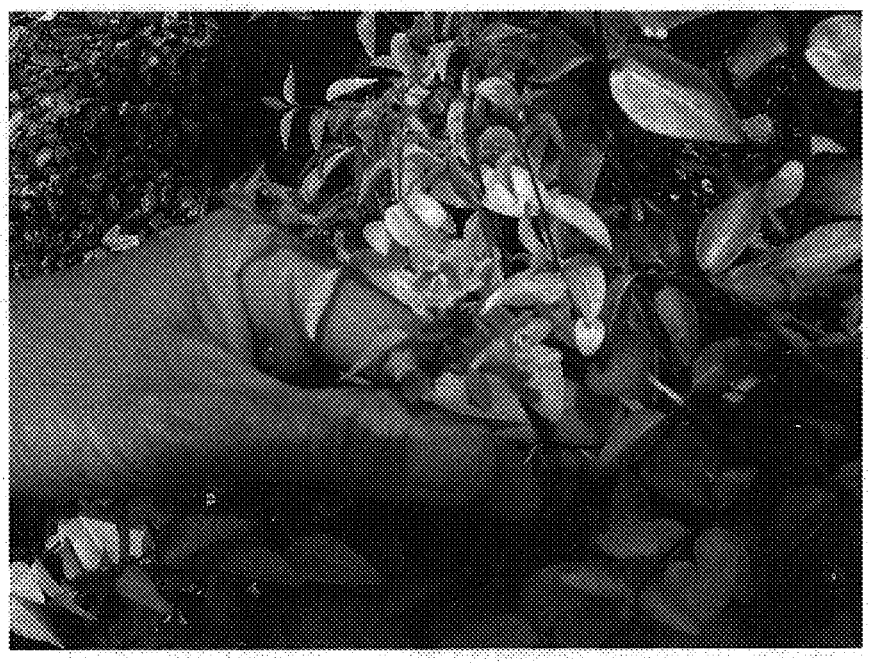

* * * * *